(12) United States Patent  (10) Patent No.: US 7,370,510 B2
Goyal  (45) Date of Patent: May 13, 2008

(54) SHOCK APPARATUS

(75) Inventor: Suresh Goyal, Warren, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 235 days.

(21) Appl. No.: 11/378,019

(22) Filed: Mar. 17, 2006

(65) Prior Publication Data
US 2007/0220950 A1  Sep. 27, 2007

(51) Int. Cl.
G01M 7/00 (2006.01)
(52) U.S. Cl. .................................. 73/12.09
(58) Field of Classification Search ............... 73/12.09
See application file for complete search history.

(56) References Cited

U.S. PATENT DOCUMENTS

| | | | |
|---|---|---|---|
| 4,006,626 A * | 2/1977 | Ruzicka et al. | 73/12.02 |
| 4,023,396 A | 5/1977 | Yakshin et al. | |
| 4,426,683 A | 1/1984 | Kissell | |
| 4,433,570 A | 2/1984 | Brown et al. | |
| 4,509,362 A * | 4/1985 | Lyons | 73/79 |
| 4,641,715 A * | 2/1987 | Stinson et al. | 173/129 |
| 4,980,526 A | 12/1990 | Reneau | |
| 5,000,030 A | 3/1991 | Umeda et al. | |
| 5,355,716 A | 10/1994 | Castelli | |
| 5,450,742 A | 9/1995 | Baltz et al. | |
| 6,308,555 B1 | 10/2001 | Liem et al. | |
| 6,374,661 B1 | 4/2002 | Buratynski et al. | |
| 6,443,013 B1 | 9/2002 | Smith et al. | |
| 6,769,287 B2 * | 8/2004 | Stewart et al. | 73/12.01 |
| 2003/0106545 A1 * | 6/2003 | Verini | 124/74 |
| 2005/0087003 A1 * | 4/2005 | Miles et al. | 73/79 |
| 2007/0220949 A1 * | 9/2007 | Goyal et al. | 73/12.04 |
| 2007/0266764 A1 * | 11/2007 | Goyal | 73/12.09 |

OTHER PUBLICATIONS

S. Goyal et al., "Shock Protection of Portable Electronic Products: Shock Response Spectrum, Damage Boundary Approach, and Beyond," Shock and Vibration, vol. 4, No. 3, pp. 169-191 (1997).
S. Goyal et al., "The Dynamics of Clattering I: Equation of Motion and Examples," J. of Dynamic Systems, Measurement, and Control, Mar. 1998, vol. 120, pp. 83-93.
S. Goyal et al., "The Dynamics of Clattering II: Global Results and Shock Protection," J. of Dynamic Systems, Measurement, and Control, vol. 120, Mar. 1998, pp. 94-102.
S. Goyal et al., "Simulation of Dynamics of Interacting Rigid Bodies Including Friction II: Software System Design and Implementation," Engineering with Computers (1994) 10, pp. 175-195.

* cited by examiner

Primary Examiner—Max Noori

(57) ABSTRACT

One embodiment of a shock apparatus comprises a plurality of impact objects spatially ordered according to decreasing mass along a substantially linear path; a guide to guide movement of the impact objects along the path; and a plurality of spacers, one spacer between each adjacent pair of impact objects in the spatial order. The guide and spacers enable a plurality of temporally ordered impacts involving the plurality of impact objects. In one embodiment, at least one of the impact objects comprises an impact portion positioned at a point where the impact object impacts at least one other impact object; and the properties of the impact portion are selectable to affect the magnitude and duration of a shock acceleration pulse experienced by the at least one impact object.

27 Claims, 10 Drawing Sheets

SHOCK APPARATUS

CROSS REFERENCE TO RELATED APPLICATION

This application is related to U.S. patent application Ser. No. 11/378,082, entitled "Rotational and Linear Shock Apparatus,", filed concurrently with the present Application, and which is hereby incorporated by reference in its entirety.

BACKGROUND OF THE INVENTION

1. Field of the Invention

The present invention generally relates to mechanical shock, and more particularly to apparatuses and methods for providing a mechanical shock.

2. Description of the Related Art

Many types of devices and structures require the ability to withstand a certain level of acceleration applied over a certain time period, i.e., a shock acceleration. Examples of such devices include micro-electro-mechanical systems (MEMs), nanodevices, photonic devices, and RF devices. Some apparatuses and methods used to deliver shock accelerations include drop testing, i.e., dropping a test object from a predetermined height; and ballistic testing, i.e., attaching the test object to a ballistic projectile which is launched by a cannon. A Split Hopkinson Bar may also be used. Such apparatuses and methods have practical limitations. For example, drop testing is limited by the height from which an object may be dropped, which in turn limits the magnitude of acceleration that may be produced. Also, ballistic methods may be undesirably dangerous and expensive.

Also, many objects need to be accelerated to a certain velocity. Examples of such objects include satellites, some types of vehicles, and ammunition. Some apparatuses and methods used to accelerate objects to a velocity include ballistic methods and attaching the test object to a rocket. One limitation of such methods is that may be undesirably dangerous and expensive.

SUMMARY OF THE INVENTION

Various deficiencies of the prior art are addressed by the present invention, one embodiment of which is a shock apparatus. In one embodiment, the shock apparatus comprises a plurality of impact objects spatially ordered according to decreasing mass along a substantially linear path; a guide to guide movement of the impact objects along the path; and a plurality of spacers, one spacer between each adjacent pair of impact objects in the spatial order. The guide and spacers enable a plurality of temporally ordered impacts involving the plurality of impact objects. In one embodiment, at least one of the impact objects comprises an impact portion positioned at a point where the impact object impacts at least one other impact object; and the properties of the impact portion are selectable to affect the magnitude and duration of a shock acceleration pulse experienced by the at least one impact object.

In one embodiment, a method comprises arranging the plurality of impact objects into the spatial order according to decreasing mass along the substantially linear path; guiding the movement of the impact objects along the path; providing a space between each adjacent pair of impact objects in the spatial order; and impacting the plurality of impact objects in a plurality of temporally ordered impacts. In one embodiment, the method comprises positioning the impact portion of at least one impact object at a point where the impact object impacts at least one other impact object; and selecting the properties of the impact portion to affect the magnitude and duration of the shock acceleration pulse experienced by the at least one impact object.

In one embodiment, the shock apparatus comprises a first impacting means for providing a velocity-changing impact involving a first impact object, the velocity-changing impact resulting in an impacted first impact object having a velocity which is changed relative to an initial velocity of the first impact object; and a second impacting means for providing an velocity-amplifying impact involving a second impact object, the velocity-amplifying impact resulting in an impacted second impact object having a velocity greater in magnitude than an initial velocity of the second impact object. In one embodiment, the shock apparatus comprises an velocity selection means for selecting the velocity produced by the velocity amplifying impact.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures.

DETAILED DESCRIPTION

Figure 1:
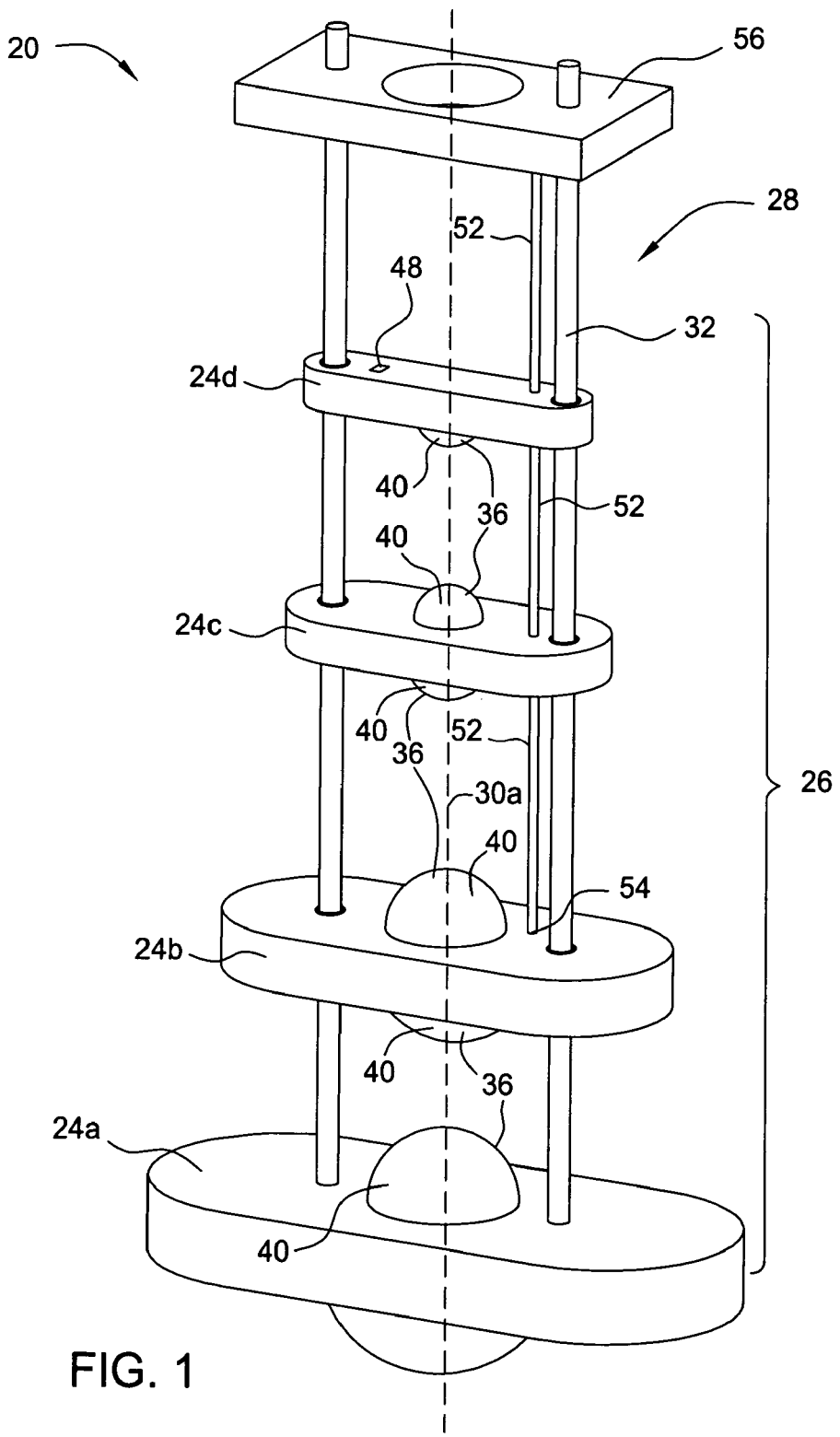
FIG. 1 depicts a perspective view of an embodiment of a shock apparatus according to the present invention.
Figure 2A:
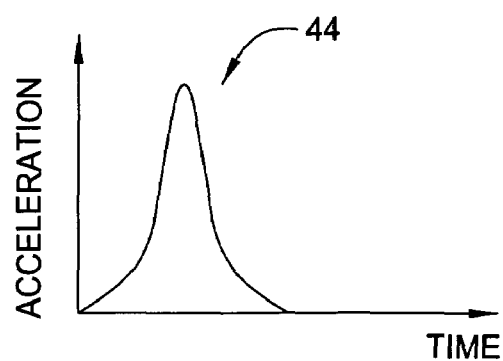
FIGS. 2a-c are graphs depicting representations of embodiments of a shock acceleration pulse delivered by an embodiment of the shock apparatus.

An embodiment of a shock apparatus 20 according to the present invention is depicted in FIG. 1. The shock apparatus 20 is capable of delivering a mechanical shock to a test object 48. The shock is an acceleration applied to the test object 48. Equivalently, the shock can be characterized as a change in velocity of the test object 48. The shock acceleration comprises an acceleration magnitude as a function of time. In one embodiment, the shock acceleration delivered by the shock apparatus 20 comprises a shock acceleration pulse 44. FIG. 2a depicts one embodiment of the shock acceleration pulse 44. In FIG. 2a, the x-axis represents time and the y-axis represents acceleration magnitude. The magnitude of the area under the curve representing the acceleration pulse 44 represents the change in velocity imparted by the shock acceleration pulse 44 to the test object 48. The shock acceleration delivered by the shock apparatus 20 may also comprise an acceleration as a function of time having a form other than that of the pulse 44.

The shock apparatus 20 comprises a plurality of impact objects 24. In one embodiment, the plurality of impact objects 24 comprise at least two impact objects 24, including a first impact object 24a and a second impact object 24b. The embodiment of the shock apparatus 20 depicted in FIG. 1 comprises four impact objects 24: the first impact object 24a, the second impact object 24b, a third impact object 24c and a fourth impact object 24d.

Figure 3A:
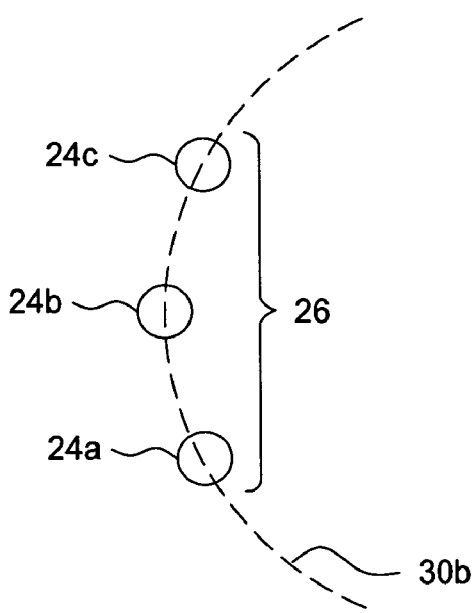
FIGS. 3a-b depict schematic views of embodiments of a path of movement of the plurality of impact objects of an embodiment of the shock apparatus.
Figure 3B:
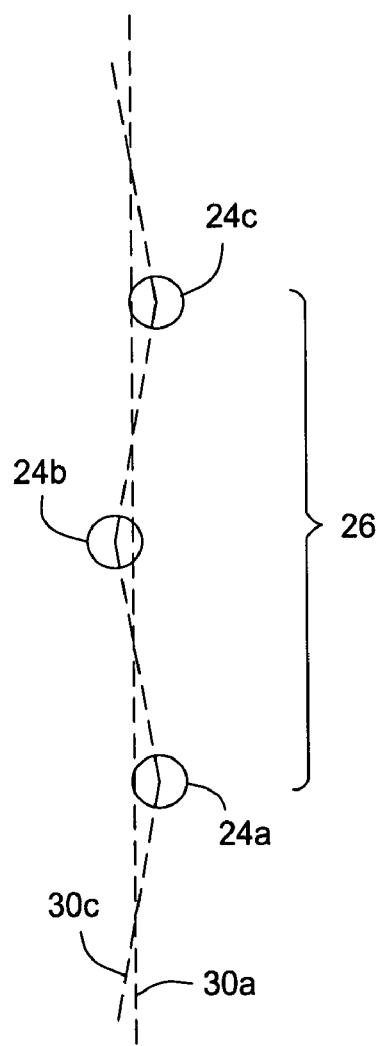

The plurality of impact objects 24 are arranged in a spatial order 26 relative to each other. In one embodiment, the plurality of impact objects 24 are arranged in a spatial order along a path 30 of movement of the impact objects 24. For example, FIG. 1 depicts an embodiment in which the spatial order 26 is a linear spatial order 26 along the path 30 which comprises a linear path 30a, i.e., a line. In FIG. 1, the impact objects 24 are arranged in the linear spatial order 26, with the first impact object 24a being first in the spatial order 26, the second impact object 24b being second in the spatial order 26, the third impact object 24c being third in the spatial order 26, and the fourth impact object 24d being fourth in the spatial order 26. Other spatial orders 26 are also possible. For example, FIG. 3a depicts an embodiment of the path 30 which comprises a curved path 30b along which the impact objects 24 are spatially ordered relative to each other. In another embodiment, the path 30 comprises a substantially linear path 30c. FIG. 3b depicts one embodiment of the substantially linear path 30c in which the substantially linear path 30c follows within a predetermined spatial distance from the linear path 30a. For example, in one embodiment, the angle between the substantially linear path 30c and the linear path 30 is no greater than about 15°. An advantage of embodiments having the linear path 30a or the substantially linear path 30c is a relatively increased efficiency of the transfer of kinetic energy between impact objects 24 in comparison to non-linear embodiments of the path 30.

Each of the plurality of impact objects 24 comprises a mass, and in one embodiment, the spatial order 26 is also an ordering of the impact objects 24 according to decreasing value of mass. For example, in one embodiment having two impact objects 24, the first impact object 24a first in the spatial order 26, the second impact object 24b second in the spatial order 26, the first impact object 24a has a first mass greater than the second mass of the second impact object 24b. In the embodiment depicted in FIG. 1, having four impact objects 24, the impact objects 24 in the spatial order are arranged according to decreasing mass moving spatially up the order 26 as depicted in FIG. 1. For example, the first impact object 24a has a first mass, the second impact object 24b has a second mass less than the first mass, the third impact object 24c has a third mass less than the second mass, and the fourth impact object 24d has a fourth mass less than the third mass.

In one embodiment, the test object 48 is attached to at least one of the plurality of impact objects 24. The test object 48 can be attached to any part of an impact object 24 and experiences the shock acceleration experienced by the impact object 24 to which it is attached. In one embodiment, the test object 48 is attached to the impact object 24 having the least mass. Depending upon the configuration of the shock apparatus 20, the impact object 24 having the least mass has the potential to experience the highest magnitude of shock acceleration. For example, in one embodiment having only two impact objects 24, the test object 48 is attached to the second impact object 24b having the second mass less than the first mass of the first impact object 24a. In the embodiment depicted in FIG. 1, the test object 48 is attached to the fourth impact object 24d having the fourth mass which is least among the plurality of masses of the plurality of impact objects 24.

The shock apparatus 20 comprises a guide 28 to guide the movement of the plurality of impact objects 24. The guide is associated with the path 30, and guides the movement of the plurality of impact objects 24 along the path 30. The guide 28 is capable of maintaining the spatial order 26 of the plurality of impact objects 24 during at least a portion of a plurality of impacts experienced by the plurality of impact objects 24 during operation of the shock apparatus 20. The impact objects 24 and the guide 28 are arranged such that impact objects 24 which are adjacent to each other in the spatial order 26 are capable of impacting each other as they move along the path 30. For example, in the embodiment depicted in FIG. 1, the second impact object 24b is capable of moving along the path 30a to impact both the first impact object 24a and the third impact object 24b. Similarly, the third impact object 24c is capable of moving along the path 30a to impact at least the second impact object 24b and the fourth impact object 24d. Similarly, the fourth impact object 24d is capable of moving along the path 30a to impact at least the third impact object 24c.

Figure 5:
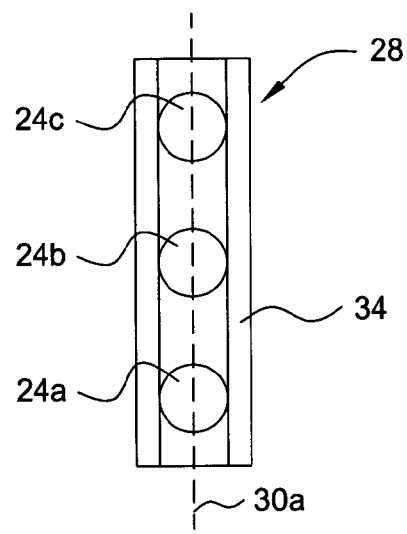
FIG. 5 depicts a sectional view of an embodiment of the guide having an enclosing structure about the plurality of impact objects.
Figure 4:
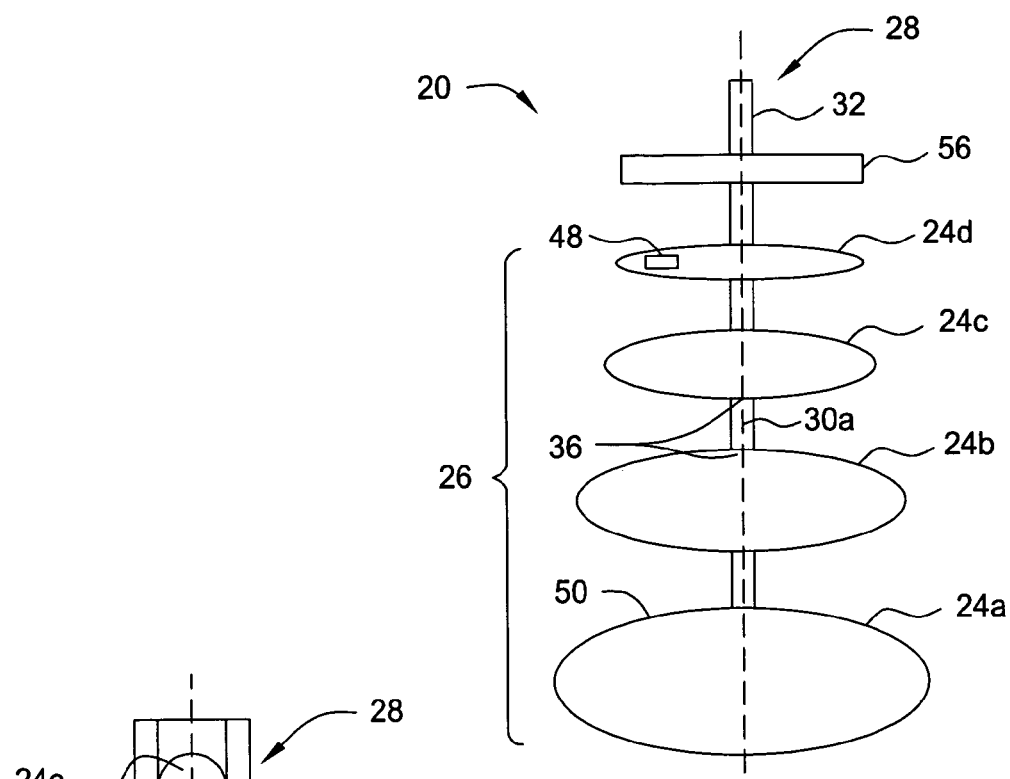
FIG. 4 depicts a front view of an embodiment of the shock apparatus having an embodiment of a guide comprising a single guide rod.

Generally speaking, the guide 28 may take a variety of forms. For example, in the embodiment depicted in FIG. 1, the guide 28 comprises two guide rods 32 arranged about the associated path 30. However, in other embodiments, the guide 28 may comprise other forms. For example, FIG. 4 depicts an embodiment of the shock apparatus 20 in which the guide 28 comprises a single guide rod 32. In another example, FIG. 5 depicts an embodiment of the guide 28 in which the guide 28 comprises a hollow cylinder 34. In other embodiments, the guide 28 may comprise other enclosing structures. The guide 28 may also comprise an electromagnetic field, or other potential field, which interacts with the impact objects 24 to guide them.

Figure 6:
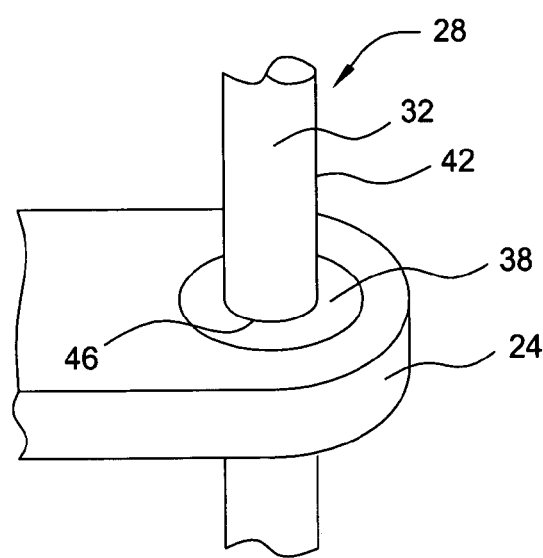
FIG. 6 depicts a partial perspective view of an embodiment of an interface between the guide and one impact object.

In one embodiment, the guide 28 comprises a surface 42 which contacts a surface 46 of the impact object 24. For example, in the embodiment depicted in FIG. 1, the second, third and fourth impact objects 24b,c,d each comprise a pair of linear bearings 38 that enable the impact objects 24 to slide along the guide rods 32 with a minimum of frictional resistance. FIG. 6 depicts a partial perspective view of the connection between the impact object 24 and the guide 28 of the embodiment of the shock apparatus 20 depicted in FIG. 1. FIG. 6 depicts the contacting surfaces 42, 26 of the guide 28 and impact object 24, and the linear bearing 38. The linear bearing 38 has a circular opening sized to accommodate the diameter of the guide rod 32.

Variation of the shape, size and weight of each of the plurality of impact objects 24 is possible. Each of the plurality of impact objects 24 comprises at least one impact portion 36 which is the portion 36 of the impact object 24 where an impact with another impact object or another object 64 (depicted in FIGS. 10a-c and FIG. 11), such as for example a fixed-position object, takes place. In one embodiment, the plurality of impact objects 24 comprise a specific impact object 24 having a shape, size, structure and material different from another specific impact object 24.

A method of using the shock apparatus 20 includes a plurality of impacts occurring in a temporal order which is related to the spatial order 26. Each of the plurality of impacts comprises at least one of: an impact between at least two impact objects 24 or an impact between at least one of the plurality of impact objects 24 and another object 64 such as the fixed position object or a non-fixed position object. Each impact is characterized by a coefficient of restitution e, which is a measure of the conservation of kinetic energy of the impact. In one embodiment, for an impact between two objects having first velocities Va1 and Vb1 before the impact and second velocities Va2 and Vb2 after the impact, the coefficient of restitution is defined by equation 1 below:

$$e=-(Vb2-Va2)/(Vb1-Va1). \quad (1)$$

For example, a completely elastic impact, with e=1, has 100% restitution and completely conserves the kinetic energy of the involved objects. A completely inelastic impact, with e=0, has 0% restitution and does not conserve the kinetic energy of the involved objects. In one embodiment of the shock apparatus 20, it is desirable to have relatively high restitution impacts in order to efficiently utilize the kinetic energy of the plurality of impact objects 24 and achieve the highest possible shock acceleration delivered to the test object 48. In one embodiment, the shock apparatus 20 enables each of the plurality of temporally ordered impacts to have an associated restitution e wherein e≧0.5.

In one embodiment, each of the plurality of temporally ordered impacts is temporally discrete from the other impacts of the plurality of temporally ordered impacts. That is, in one embodiment, none of the plurality of temporally ordered impacts has a temporal duration which overlaps the temporal duration of any of the other impacts.

Figure 2B:
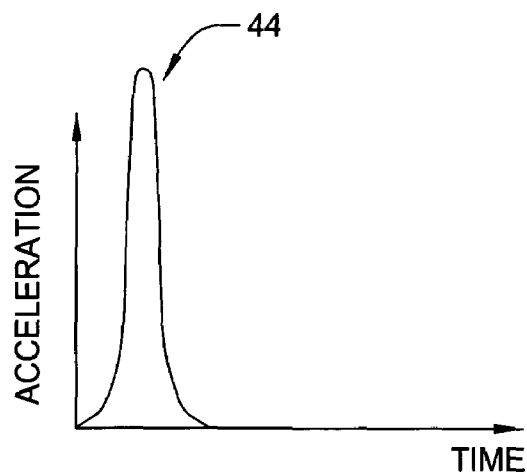
Figure 2C:
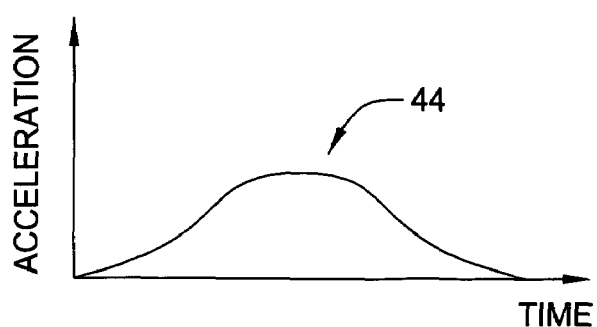

In one embodiment, the properties of the shock acceleration produced by each impact are determined by selecting the material and structural properties of the impact objects 24 involved in the impact and the impact portions 36 thereof. For example, in one embodiment, the properties of the impact portion 36 are selected to shape the shock acceleration pulse 44. In the embodiment of the shock acceleration pulse 44 depicted in FIG. 2a, the pulse 44 has a representative height and width. FIG. 2b depicts another embodiment of the shock acceleration pulse 44 in which, while maintaining the same area under the pulse 44, the height may be increased and the width decreased, i.e., the peak acceleration magnitude increased and the duration of the pulse 44 decreased. FIG. 2c depicts another embodiment of the shock acceleration pulse 44 in which, while maintaining the same area under the pulse 44, the height may be decreased and the width increased, i.e., the peak acceleration magnitude decreased and the duration of the pulse 44 increased.

In one embodiment, to provide an impact having a relatively increased acceleration magnitude, at least one of the material or structure of the impact portion 36 is selected to provide an elastic response having a relatively short time constant which enables the impact to produce a shock acceleration having a relatively higher magnitude and shorter duration. Examples of materials that are suitable for producing these relatively short time constant elastic impacts include impact portions 36 comprising relatively harder elastic materials such as, for example, metals, hard plastics, quartz, diamonds, etc. In one embodiment, it is desirable for the impact involving the test object 48, e.g., the impact involving the impact object 24 to which the test object 48 is attached, to experience acceleration as high in magnitude as possible. Thus, in one embodiment, the materials and structures described in this paragraph are used especially for the impact portions 36 involved in this impact.

In one embodiment, to provide an impact having a relatively decreased acceleration magnitude, at least one of the material or structure of the impact portion 36 is selected to provide an elastic response having a relatively longer time constant which enables the impact to produce a shock acceleration having a relatively lower magnitude and longer duration. Examples of materials that are suitable for producing these relatively longer time constant elastic impacts include impact portions 36 comprising relatively softer elastic materials such as, for example, elastomers, foams, rubber, etc. In one embodiment, it is not necessary for the impacts not involving the impact object 24 to which the test object 48 is attached to experience accelerations as high in magnitude as possible, and thus the emphasis can instead be placed on achieving as high a restitution as possible. Thus, in one embodiment, the materials and structures described in this paragraph are used for the impact portions 36 not involved in the impact involving the test object 48.

Figure 7:
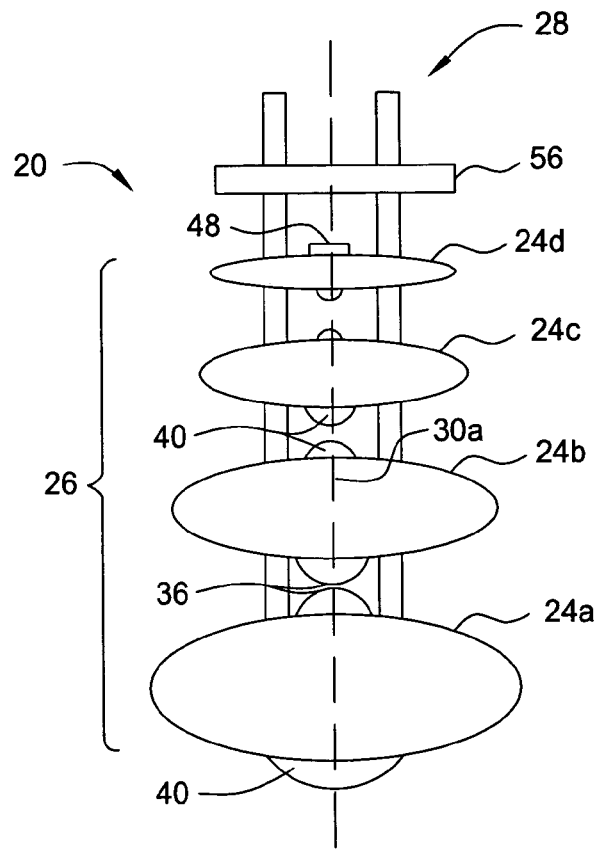
FIG. 7 depicts a front view of an embodiment of the shock apparatus having at least one impact object having an impact portion comprising a protrusion.

In one embodiment, the impact portion 36 comprises a protrusion 40 from the impact object 24. FIG. 7 depicts an embodiment of the shock apparatus 20 in which at least one of the plurality of impact objects 24 have at least one protrusion 40. In one embodiment, the selecting of the material and structural properties of the impact portion 36 to determine the properties of the shock acceleration produced by the impact includes selecting the material and structural properties of the protrusion 40. In one embodiment, the protrusion 40 has material and structural properties which are different from another part of the impact object 24.

In the embodiment depicted in FIG. 1, the impact objects 24 each in part comprise a plate. Also, in the embodiment depicted in FIG. 1, each of the impact objects 24 has an impact portion 36 comprising at least part of a hemispherical protrusion 40 from the plate. The size, thickness and material of the plates are selected to provide the predetermined mass for each of the impact objects 24. In one embodiment, the impact object 24 is at least partially hollow and has internal structures which are selected to determine the stiffness of the impact portion 36. Also, progressively greater hollowing of each successive impact object 24 in the plurality of spatially ordered impact objects 24 can be used to achieve the decreasing mass of the impact objects 24 in the spatial order 26. In one embodiment, the impact object is 24 constructed such that different hemispherical protrusions 40 are interchangeable in a given impact object 24 to allow a user to vary the shock acceleration properties of an impact, and determine the overall operating characteristics of the shock apparatus 20.

In one embodiment, one of the plurality of impact objects 24 may be fixedly attached to the guide 28. For example, in the embodiment of the shock apparatus 20 depicted in FIG. 1, the first impact object 24a is fixedly attached to the guide 28. Thus, in this embodiment, the mass of the first impact object 24a comprises the mass of the guide 28. In the embodiment depicted in FIG. 1, the guide 28 also comprises an end stop 56, e.g., a top or end plate 56, which constrains the movement of the plurality of impact objects from leaving the guide 28 and the path 30 associated therewith. That is, the end stop 56 constrains the plurality of impact objects 24 to movement along a predetermined length of the path 30. The end stop 56 can comprise a means to allow a gentle impact between the end stop 56 and the final impact object 24, such as for example a spring or padding.

In one embodiment, at least some of the impact portions 36 of the plurality of impact objects 24 comprise a curved surface 50. FIG. 4 depicts an embodiment of the shock apparatus 20 in which the impact portions 36 of each of plurality of impact objects 24 comprise the curved surface 50. In the embodiment depicted in FIG. 4, the impact object 24 has a curved cross-sectional profile having the curved surface 50. Other shapes are also possible for the curved surface 50. In one embodiment, the impact portion 36 comprising the curved surface 50 provides desirable propagation characteristics of the shock acceleration through the impact object 24 and also shapes the shock acceleration pulse 44 as discussed above. For example, in one embodiment an impact portion 36 comprising the curved surface 50 is used to increase the restitution of an impact.

In one embodiment, the shock apparatus 20 comprises at least one spacer 52 between a pair of adjacent impact objects 24. The spacer 52 has a predetermined length and acts to separate the impact objects 24 before and until the time of impact between the adjacent impact objects 24. In one embodiment, the shock apparatus 20 comprises a plurality of spacers 52 between a plurality of pairs of adjacent impact objects 24 or between each pair of adjacent impact objects 24. The plurality of spacers 52 acts to separate the plurality of impact objects 24 from their adjacent impact object 24 in order to maintain the desired temporal order of impacts among the plurality of impact objects 24.

Figure 8A:
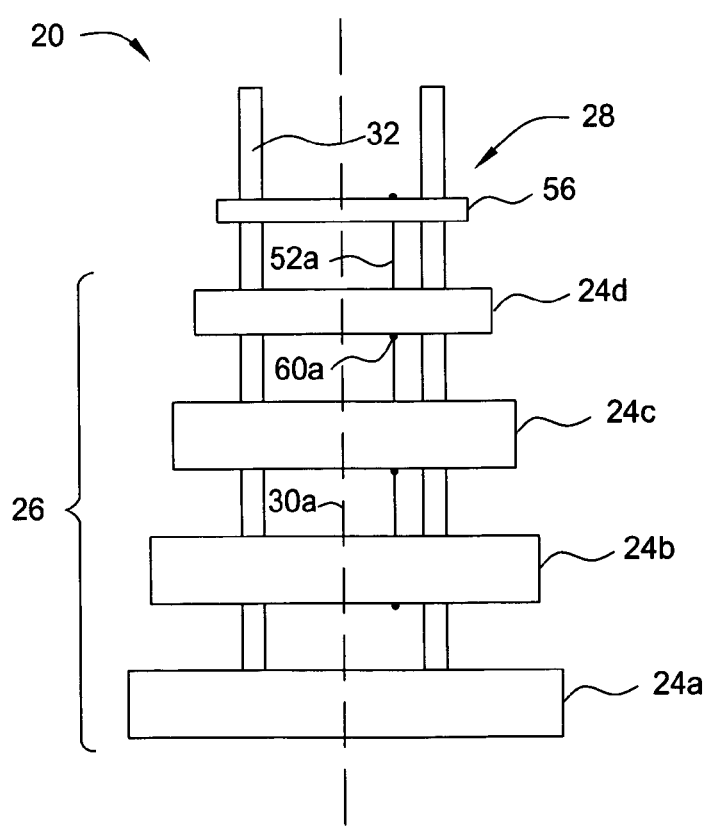
FIGS. 8a-b depict a front views of embodiments of the shock apparatus comprising embodiments of a spacer.

The spacer 52 may comprise any suitable apparatus or means to create the desired predetermined distance between impact objects 24. For example, FIG. 8a depicts one embodiment in which the spacer 52 comprises a relatively thin string 52a attached to the top plate 56. The string 52a in turn passes through each impact object 24 as it travels downward in FIG. 8a, for example, through a hole 54 (shown in FIG. 1) or a notch in the impact object 24. In one embodiment, the spacer 52 has an obstruction 60, e.g. a knot 60a in the string 52a, after it passes through each impact object 24, thereby creating an interaction between the string 52a and the impact objects 24 such that each of the impact objects 24 is suspended by the string 52a at a predetermined distance from the impact object 24 above it. The properties of the string 52a are selected such that the string 52a is strong enough to suspend and space the impact objects 24, but weak enough, or weakly enough attached to the top plate 56, to break free from the top plate 56 at the appropriate moment during the use of the shock apparatus 20 in order to enable the plurality of impacts. In another embodiment, instead of the string 52a, the spacer 52 may comprises another type of material or structure, other than a string, passing through the impact objects 24 to suspect the impact objects 24.

Figure 8B:
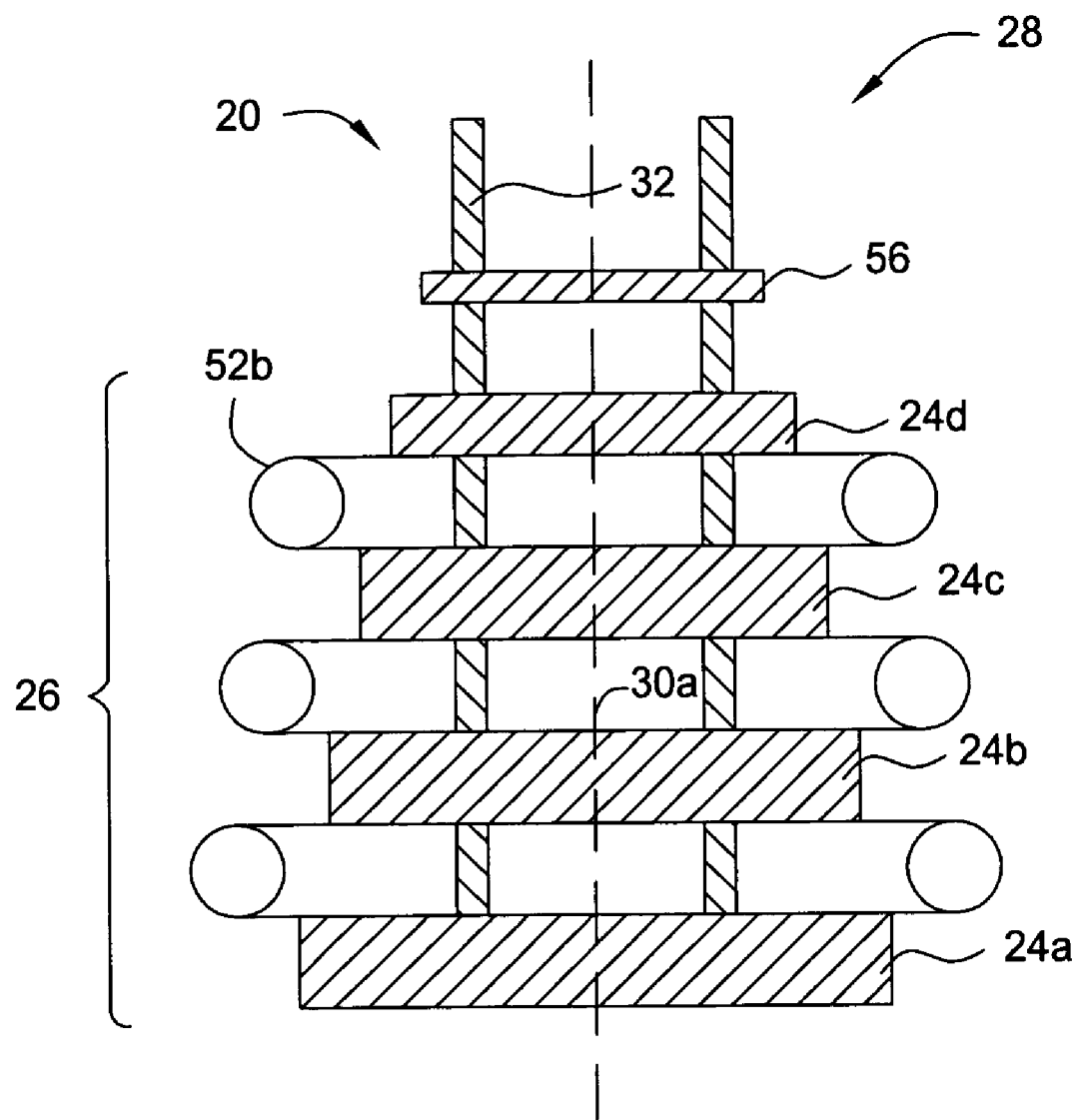

In one embodiment the spacer 52 comprises a spring 52b or other compressible object. For example, FIG. 8b depicts an embodiment of the shock apparatus 20 comprising springs 52b positioned between each impact object 24. The compression characteristics, e.g., the spring constant, of the springs 52b are selected such that they maintain suitable separation between the impact objects 24 at rest or traveling together at a first set of velocities, e.g. similar velocities, but compress under a second set of velocities, i.e. different velocities or the presence of an acceleration differential, thus allowing the impact objects 24 to impact each other at the appropriate moments during use of the shock apparatus 20. In one embodiment, the spacer 52 comprises a compressible object other than a spring 52b.

In one embodiment, the spacer 52 uses an electromagnetic means such as, for example, a solenoid to maintain the predetermined distance between the impact objects 24. For example, in one embodiment the spacer 52 comprises a solenoid.

In one embodiment, instead of a separate spacer 52, the impact object 24 comprises an integral structure or portion which achieves a similar function. For example, in one embodiment, the impact object 24 comprises a compressible portion which maintains a separation distance between less compressible portions of the impact objects 24, other portions of the impact objects 24, or both. In such an embodiment, there is no need for a spacer 52 which is a separate object from the impact object 24. Instead, the compressible portion provides a similar function by separating the less compressible or other portions prior to the impact. For example, FIG. 11, which is discussed in more detail below, depicts an embodiment of the shock apparatus 20 comprising impact objects 24 having protrusions 40 but not separate spacers 52. In one embodiment of the shock apparatus 20 which does not have separate spacers 52, the shock apparatus 20 is arranged so that there is complete restitution of impact objects 24 between successive impacts in the temporally ordered plurality of impacts. For example, the material and structure of the impact objects 24, including the impact portions 36, can be selected to ensure complete restitution of the impact objects 24 involved in a given impact before the next impact in the plurality of temporally ordered impacts occurs.

The operation of the shock apparatus 20 can be understood in part by examining the effect of varying the relative masses of two impact objects 24 involved in an impact. FIG. 9a-e depict moments in time of various scenarios before and after an impact between two impact objects 24 in which the ratio of the masses of the impact objects 24 is varied across the scenarios. The scenarios depicted in FIGS. 9a-e assume that impacts realize 100% restitution. The understanding gained by examining the scenarios depicted in FIGS. 9a-e is believed to be nonetheless relevant to relatively high, yet non-100%, restitution impacts. The scenarios depicted in FIGS. 9a-e are also depicted horizontally, thus removing the effect of gravity. Again, the understanding gained by examining by the scenarios depicted in FIGS. 9a-e is believed to be nonetheless also relevant to embodiments of the shock apparatus 20 positioned vertically, e.g., as depicted in FIG. 1, as gravitational acceleration typically has a magnitude which is relatively small in comparison to other accelerations produced by the shock apparatus 20.

Figure 9A:
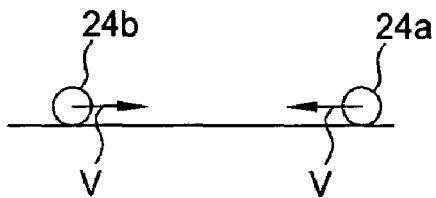
FIGS. 9a-e depict embodiments of various moments in time before and after an impact between two impact objects.

FIG. 9a depicts an initial moment in time in which two impact objects 24 are traveling towards each other before an impact. The first and second impact objects 24a,b each having a velocity of magnitude V, but in opposite directions. FIG. 9b-e depict different scenarios of a moment in time after the impact between the first and second impacts 24a,b objects depicted in FIG. 9a in which the ratio of the masses of the impact objects 24a,b is varied.

Figure 9B:
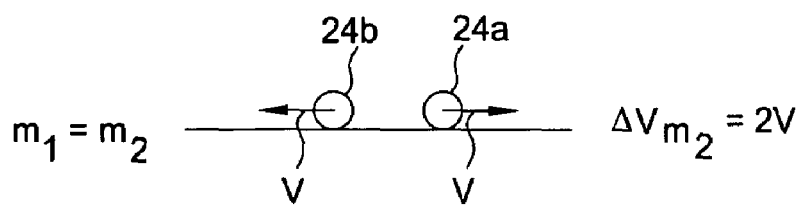

FIG. 9b depicts a scenario in which the first mass, m1, of the first impact object 24a and the second mass, m2, of the second impact object 24b, are equal, i.e., m1=m2. In this scenario, after the impact both impact objects 24a,b travel away from each other in opposite directions, each having a new velocity having magnitude V equal to the initial velocity magnitude but in the opposite direction relative to the initial velocity directions. Thus, in this scenario, both impact objects 24a,b experience a change in velocity ΔV in which ΔV=2V.

Figure 9C:
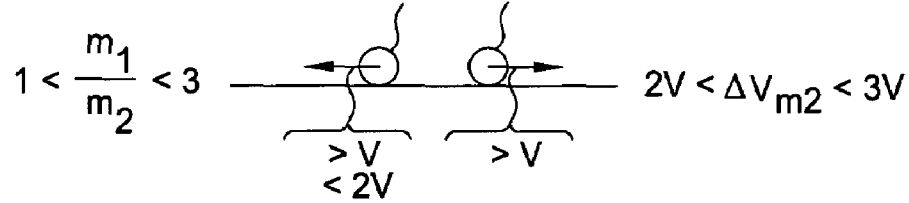

FIG. 9c depicts a scenario in which 1<m1/m2<3. In this scenario, after the impact, the second impact object 24b travels away from the first impact object 24a at a velocity V2 in the opposite direction from its initial velocity and having a value in which V<V2<2V. The first impact object 24a travels away from the second impact object 24b at a velocity V1 in which V1<V in a direction opposite to its initial velocity. Thus, in this scenario the second impact object 24b experiences a change in velocity ΔVm2 in which 2V<ΔVm2<3V.

Figure 9D:
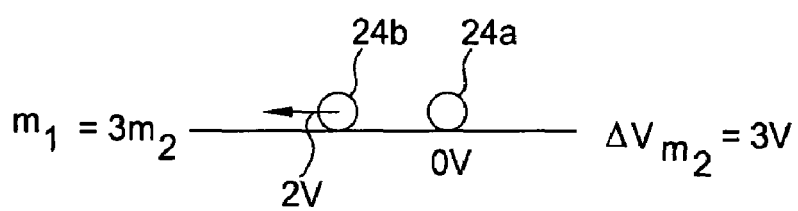

FIG. 9d depicts a scenario in which m1=3 m2. In this scenario, after the impact, the second impact object 24b travels away from the first impact object 24a at a velocity V2 in the opposite direction from its initial velocity and having a magnitude in which V2=2V. The first impact object 24a comes to a rest after the impact. Thus, in this scenario the second impact object 24b experiences a change in velocity ΔVm2 in which ΔVm2=3V.

Figure 9E:
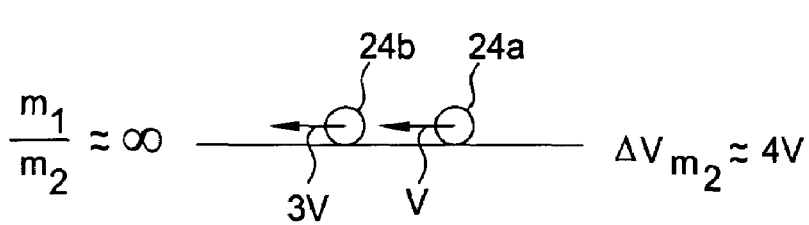

FIG. 9e depicts a scenario in which m1/m2≈∞. In this scenario, after the impact both impact objects 24a,b move towards the left in FIG. 9e, with the second impact object 24b traveling at a velocity V2≈3V in a opposite direction from the direction of its initial velocity. The first impact object 24a will travel at approximately the same velocity V in the same direction as the direction of its initial velocity. Thus, in this scenario, the second impact object 24b experiences change in velocity ΔVm2 in which ΔVm2≈4V.

From the scenarios depicted in FIGS. 9a-e, it can be understood that a special regime of velocity acceleration of the second impact object 24b exists which efficiently utilizes the momentum of the first impact object 24a. Particularly, in the embodiments in which the first mass has a value which is at least 3 times the value of the second mass, e.g., the embodiments depicted in FIGS. 9d-e, the first impact object 24a is not turned back. This indicates special regime of velocity acceleration relative to the scenarios depicted in FIGS. 9b-c. Thus, in one embodiment of the shock apparatus 20, the ratio of masses of adjacent impact objects 24 in the spatial order 26 is greater than or equal to 3. For example, in one embodiment having two impact objects 24, the ratio of the first mass of the first impact object 24a to the second mass of the second impact object 24b has a value in which m1/m2≧3. In one embodiment having more than two impact objects 24, the ratios of the masses of adjacent impact objects 24 have values in which m1/m2≧3, m2/m3≧3, m3/m4≧3, etc., wherein m3 is the mass of the third impact object 24c, m4 is the mass of the fourth impact object 24d, etc. However, although the regime in which m1/m2≧3 marks a special regime of operation of the shock apparatus 20, velocity acceleration nonetheless still occurs for m1>m2, and thus in one embodiment, as discussed above, the first mass is simply greater than the second mass. Similarly, in one embodiment having more than two impact objects 24, the masses have values according to m1>m2, m2>m3, m3>m4, etc.

Figure 10A:
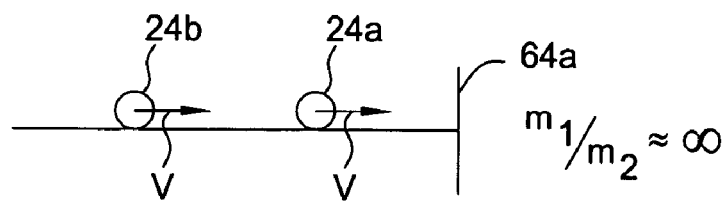
FIGS. 10a-c depict embodiments of various moments in time before and after a plurality of impacts involving a first and second impact object and a fixed-position object.
Figure 10B:
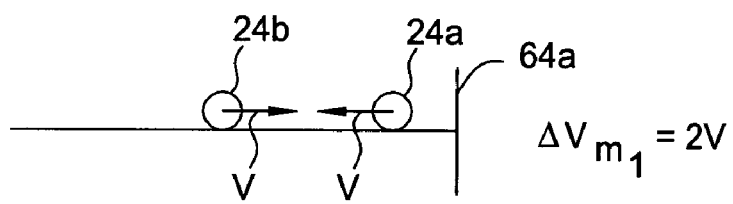
Figure 10C:
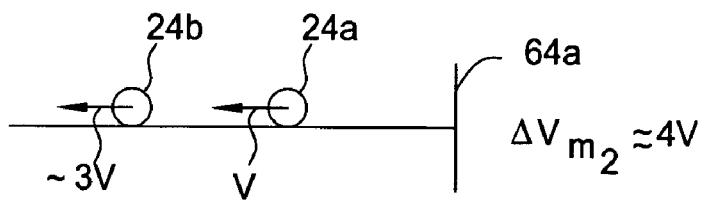

The operation of the shock apparatus 20 can be further understood by examining the cumulative velocity acceleration of a plurality of impacts between impact objects 24. FIGS. 10a-c depict an embodiment of various moments in time of an impact scenario between two impact objects 24 and the other object 64, which in the depicted scenario is a fixed position object 64a. In the scenarios depicted in FIGS. 10a-c, the ratio of the mass of the first impact object 24a to the mass of the second impact object 24b is assumed to be infinite, i.e., m1/m2≈∞. The understanding gained by examining the scenarios depicted in FIGS. 10a-c is believed to be nonetheless relevant to impacts between impact objects 24 having non-infinite mass ratios. As with FIGS. 9a-e, the scenarios depicted in FIGS. 10a-c assume that impacts realize 100% restitution. The understanding gained by examining the scenarios depicted in FIGS. 10a-c is believed to be nonetheless relevant to relatively high yet non-100% restitution impacts.

FIG. 10a depicts an embodiment of an initial moment in time in which two impact objects 24 are moving towards the fixed position object 64a, e.g., a wall. In the moment of time depicted by FIG. 10a, both impact objects 24 have a velocity having the same magnitude V in the same direction towards the fixed position object 64a.

FIG. 10b depicts a moment in time after the first impact object 24a impacts the fixed-position object 64a. In the moment in time depicted by FIG. 10b, the first impact object 24a has reversed its direction, while retaining the same velocity magnitude V, but moving in the opposite direction relative to its initial direction. The second impact object 24b is moving towards the first impact object 24a, which is now moving towards the second impact object 24b, and they both have the same velocity magnitude V, although in different directions. The moment in time depicted by FIG. 10b is before the first impact object 24a impacts the second impact object 24b.

FIG. 10c depicts moment in time after the second impact object 24b impacts the first impact object 24a. After the impact between the first and second impact objects 24a,b, the second impact object 24b has a velocity magnitude≈3V in a direction opposite to its initial direction. The first impact object 24a has roughly the same velocity in the same direction as it does in FIG. 10b, due to its roughly infinite mass. The degree to which the first impact object 24a retains its original velocity magnitude V is related to the degree to which the mass ratio of the first mass to the second mass is infinite. As the mass ratio becomes more finite, the first impact object 24a loses some of its initial velocity magnitude after the impact with the second impact object 24b.

The depictions of FIGS. 10a-c demonstrate velocity acceleration achieved by impact objects 24 in embodiments of the shock apparatus 20. The first impact object 24a experiences, as a result of the impact between the first impact object 24a and the fixed-position object 64a, a change of velocity ΔVm1 in which ΔVm1=2V. The second impact object 24b experiences, as a result of the impact between the second impact object 24b and the first impact object 24a, a change of velocity ΔVm2 in which ΔVm2=4V. Thus, each impact in a plurality of temporally ordered impacts between a plurality of impact objects 24 produces a cumulatively increasing velocity acceleration. Generally speaking, in a scenario in which there is an infinite mass ratio between adjacent impact objects 24, a succession of impacts between N impact objects 24 will produce an overall change in velocity ΔV of the lastly impacted impact object 24 in which $\Delta V = 2^N V$, V being the common initial velocity V of the impact objects 24. This $\Delta V = 2^N V$ change in velocity results if all of the impacts occur in the proper order, i.e., each impact occurring individually in a temporal order related to the spatial order 26 of the plurality of impact objects 24. Specifically, the correct temporal order is as follows: the first impact object 24a impacts the fixed-position object 64a, then the impacted first impact object 24a impacts the unimpacted second impact object 24b, then the impacted second impact object 24b impacts the unimpacted third impact object 24c, then the impacted third impact object 24c impacts the unimpacted fourth impact object 24d, etc.

For example, if there are one impact object 24 and the fixed position object 64a, the change in velocity has a value $\Delta V$ in which $\Delta V=2^1 V=2V$. If there are two impact objects 24 and the fixed position object 64a, the change in velocity has a value $\Delta V$ in which $\Delta V=2^2 V=4V$. If there are three impact objects 24 and the fixed-position object 64a, the change in velocity has a value $\Delta V$ in which $\Delta V=2^3 V=8V$. If there are four impact objects 24 and a fixed-position object 64a, the change in velocity has a value $\Delta V$ in which $\Delta V=2^4 V=16V$.

Embodiments of the shock apparatus 20 enable the plurality of impacts between the plurality of impact objects 24 to occur in the proper temporal order. A relatively high acceleration is thus enabled in part by the velocity amplification of the plurality of impacts. This provides one advantage of the present invention over other methods and apparatuses in that it enables a high acceleration in a relatively contained and safe apparatus. The plurality of impacts enabled by the present invention may be described, from one perspective, as spatially folded. That is, the shock apparatus 20 achieves an acceleration magnitude that would require the test object 48 be dropped from an impractically large height in a drop testing method or apparatus to achieve comparable acceleration magnitudes. The shock apparatus 20 of the present invention instead achieves the same result in a much smaller space, and thus could be considered to be spatially folded in comparison to the larger space required by drop testing. Similarly, to achieve comparable acceleration magnitudes by ballistic methods would be undesirably dangerous and expensive.

In one embodiment, the other object 64 does not have a fixed position, and instead is a variable position object. For example, the other object 64 can have a velocity in a direction moving towards the first impact object 24a.

In one embodiment, the shock apparatus 20 does not comprise an end stop 56, and the last and lightest impact object 24 in the spatial order of the plurality of impact objects 24 is instead launched from the shock apparatus 20 at a velocity which is a result of the shock applied to the last impact object 24. In this embodiment, the test object 48 can be the last impact object 24 or can be attached to the last impact object 24.

In one embodiment, the test object 48 is instead attached to the end stop 56, or another similarly-positioned or fixed-position object, and the last impact object 24 impacts the test object 48.

In one embodiment of a method of using the shock apparatus 20, the plurality of impact objects 24 are provided with a predetermined initial velocity. For example, in one embodiment, the shock apparatus 20 is dropped from a height towards the other object 64. In such an embodiment, the plurality of impact objects 24 are provided with the predetermined initial velocity at least by the acceleration of gravity. In one embodiment, the plurality of impact objects 24 are only initially accelerated by gravity.

Figure 11:
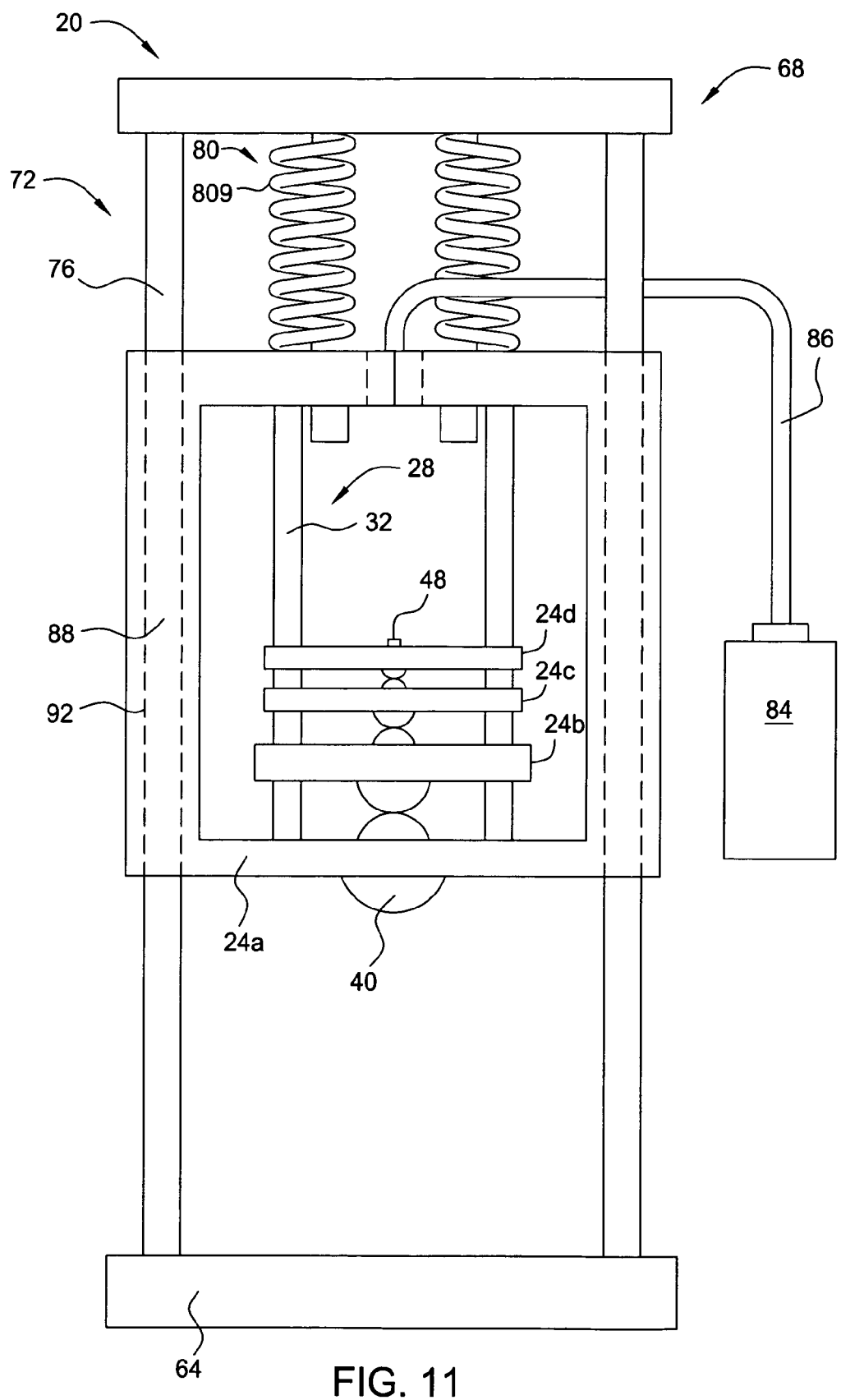
FIG. 11 depicts an embodiment of the shock apparatus comprising an embodiment of a launcher.

In one embodiment, the shock apparatus 20 comprises a launcher 68 which provides the predetermined initial velocity to the plurality of impact objects 24. The launcher 68 may comprise a variety of forms. FIG. 11 depicts one embodiment of the shock apparatus 20 comprising the launcher 68. The launcher 68 comprises a propelling means 80. For example, in the embodiment depicted, the propelling means 80 comprises a launcher spring 80a. The launcher spring 80a is compressed and calibrated to provide the predetermined initial velocity to the plurality of impact objects 24.

The launcher spring 80a is not the only possible propelling means, however. In another embodiment, the propelling means 80 comprises a ballistic means, such as, e.g., a canon.

In one embodiment, the propelling means 80 comprises a gas source. For example, in one embodiment a pressurized gas source is focused about the plurality of impact objects 24 to provide the predetermined initial velocity. The gas source also optionally comprises a heated gas. In one embodiment, the propelling means 80 comprises a magnetic propelling means having a magnet comprising at least one of: a permanent magnet, an electromagnet, or a superconducting magnet. The magnetic propelling means is arranged to provide a magnetic field about at least one of the plurality of impact objects 24.

In the embodiment depicted in FIG. 11, the launcher 68 comprises a launcher guide 72 to guide the movement of the plurality of impact objects 24 in the launcher 68. For example, in the embodiment depicted, the launcher guide 72 comprises at least one launcher guide rod 76. However, in other embodiments, other forms of the launcher guide 72 are possible. In one embodiment, the plurality of impact objects 24 or the guide 28 comprises an interface 88 to the launcher 68. For example, in the embodiment depicted in FIG. 11, the interface 88 comprises a surface 92 of the first impact object 24a which couples to the launcher guide 72.

In one embodiment, the propelling means 80 is external to the plurality of impact objects 24. For example, in some embodiments, any of the propelling means 80 discussed above can be external to the plurality of impact objects 24 and arranged to provide a force to at least one of the plurality of impact objects 24 to accelerate the plurality of impact objects 24 to the predetermined initial velocity.

In one embodiment, the propelling means 80 is internal to at least one of the plurality of impact objects 24. For example, in some embodiments, any of the propelling means 80 discussed above may be entirely or partially internal to at least one of the plurality of impact objects 24 and arranged to provide a force from the at least one of the plurality of impact objects 24 to the environment about the at least one of the plurality of impact objects 24 to accelerate the plurality of impact objects 24 to the predetermined initial velocity.

In one embodiment, at least some of the plurality of impact objects 24 are not provided with an initial velocity.

In one embodiment, the shock apparatus 20 comprises a camera 84 to record a visual record of the application of the shock acceleration provided to the test object 48. In one embodiment, the camera 84 is fixedly attached to at least one of the plurality of impact objects 24, and moves along with the at least one of the plurality of impact objects 24. In another embodiment, as depicted in FIG. 11, the camera 84 has a fixed position relative to the earth, and is attached to the at least one of the plurality of impact objects 24 by a flexible feed 86. In another embodiment, the camera 84 has a fixed position, but does not require a flexible feed 86, and instead records a fixed point in space in which an impact is known to occur by design of the shock apparatus 20.

Figure 12:
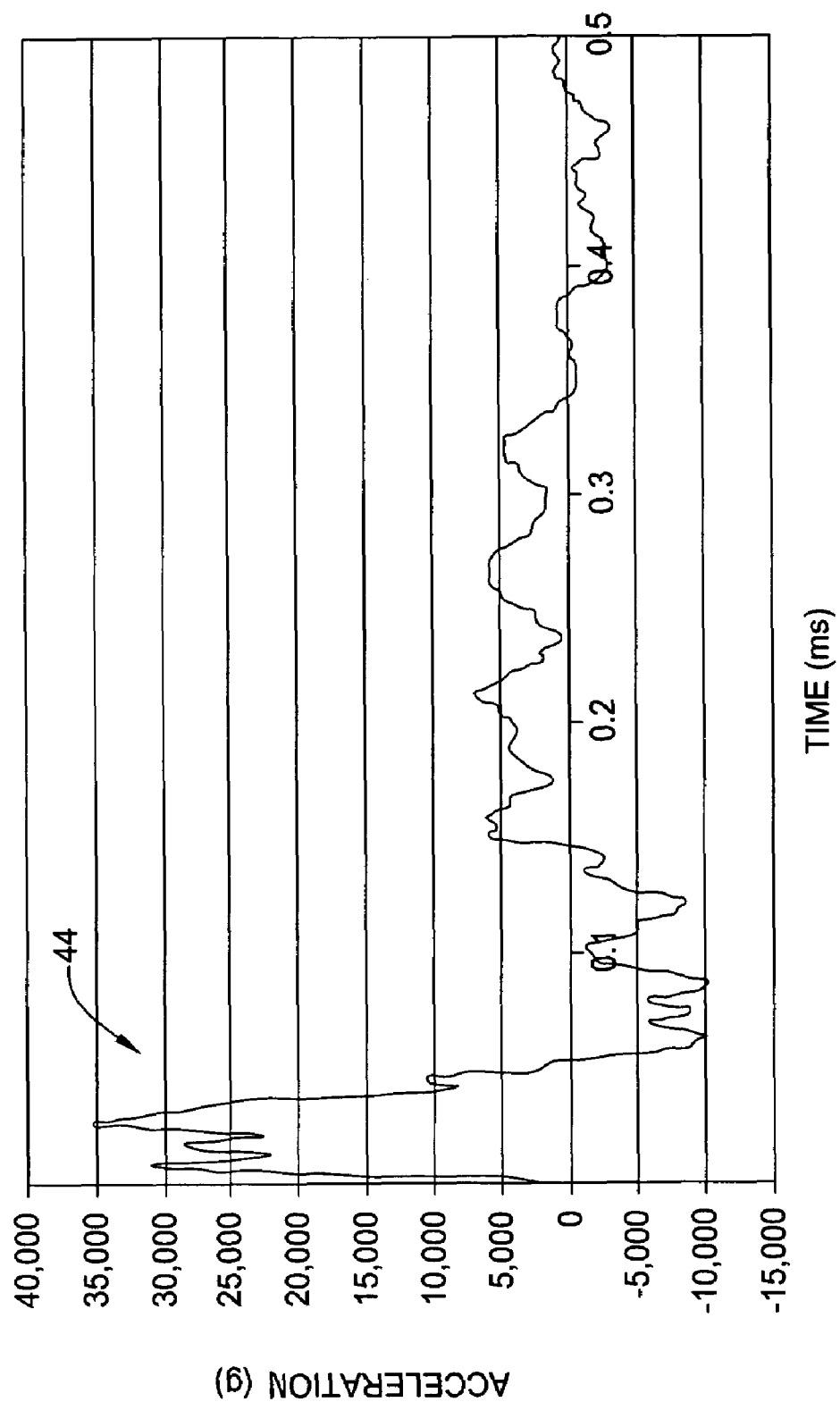
FIG. 12 is a graph depicting experimental results of shock accelerations produced by an embodiment of the shock apparatus.

FIG. 12 is a graph depicting experimental results showing shock accelerations achieved by the shock apparatus 20.

While the foregoing is directed to embodiments of the present invention, other and further embodiments of the invention may be devised without departing from the basic scope thereof, and the scope thereof is determined by the claims that follow. Various embodiments presented herein, or portions thereof, may be combined to create further embodiments. Furthermore, terms such as top, side, bottom, front, back, and the like are relative or positional terms and are used with respect to the exemplary embodiments illustrated in the figures, and as such these terms may be interchangeable.

The invention claimed is:

1. A shock apparatus, comprising:
   a plurality of impact objects spatially ordered according to decreasing mass along a substantially linear path;
   a guide to guide movement of the impact objects along the path; and
   a plurality of spacers, one spacer between each adjacent pair of impact objects in the spatial order;
   wherein the guide and spacers enable a plurality of temporally ordered impacts involving the plurality of impact objects.

2. The shock apparatus of claim 1, wherein at least one impact object comprises an impact portion positioned at a point where the impact object impacts at least one other impact object; and
   wherein the properties of the impact portion are selectable to affect the magnitude and duration of a shock acceleration pulse experienced by the at least one impact object.

3. The shock apparatus of claim 2, wherein the properties of the impact portion which are selected include the hardness and elasticity of the impact portion.

4. The shock apparatus of claim 2, wherein the impact portion comprises at least one of: a protrusion from the impact object or a curved surface of the impact object.

5. The shock apparatus of claim 1, wherein the impact object having the greatest mass is fixedly attached to the guide.

6. The shock apparatus of claim 1, wherein the guide comprises an end stop to constrain the movement of the impact objects to only along a predetermined length of the substantially linear path.

7. The shock apparatus of claim 1, comprising a test object attached to the impact object having the least mass.

8. The shock apparatus of claim 1, wherein for each pair of adjacent impact objects in the spatial order, one of the impact objects comprises a mass greater than 3 times the mass of the other impact object.

9. The shock apparatus of claim 1, wherein at least one of the plurality of impact objects comprises a surface which slides along a surface of the guide.

10. The shock apparatus of claim 1, wherein the guide comprises at least one guide rod, and at least one of the plurality of impact objects comprises at least one linear bearing.

11. The shock apparatus of claim 1, comprising a launcher to provide the plurality of impact objects with a predetermined initial velocity.

12. A method, comprising:
    arranging a plurality of impact objects into a spatial order according to decreasing mass along a substantially linear path;
    guiding the movement of the impact objects along the path;
    providing a space between each adjacent pair of impact objects in the spatial order; and
    impacting the plurality of impact objects in a plurality of temporally ordered impacts.

13. The method of claim 12, comprising:
    positioning an impact portion of at least one impact object at a point where the impact object impacts at least one other impact object; and
    selecting the properties of the impact portion to affect the magnitude and duration of a shock acceleration pulse experienced by the at least one impact object.

14. The method of claim 13, wherein the selecting the properties of the impact portion comprises selecting the hardness and elasticity of the impact portion.

15. The method of claim 13, wherein the positioning the impact portion comprises positioning at least one of: a protrusion from the impact object or a curved surface of the impact object.

16. The method of claim 12, comprising:
    fixedly attaching the impact object having the greatest mass to the guide.

17. The method of claim 12, comprising:
    constraining the movement of the impact objects to only along a predetermined length of the substantially linear path.

18. The method of claim 12, comprising:
    attaching a test object attached to the impact object having the least mass.

19. The method of claim 12, wherein the arranging of the plurality of impact objects into a spatial order according to decreasing mass comprises arranging each pair of adjacent impact objects such that one of the impact objects in the adjacent pair comprises a mass greater than 3 times the mass of the other impact object.

20. The method of claim 12, comprising:
    sliding a surface of at least one of the impact objects along a surface of the guide.

21. The method of claim 12, comprising:
    providing at least one guide rod of the guide, and at least one linear bearing of at least one of the plurality of impact objects.

22. The method of claim 12, comprising:
    dropping the plurality of impact object toward a fixed-position object, thereby allowing the plurality of impact objects to be accelerated by gravity.

23. The method of claim 12, comprising:
    providing the plurality of impact objects with a predetermined initial velocity.

24. A shock apparatus, comprising:
    first impacting means for providing a velocity-changing impact involving a first impact object, the velocity-changing impact resulting in an impacted first impact object having a velocity which is changed relative to an initial velocity of the first impact object; and
    second impacting means for providing a velocity-amplifying impact involving a second impact object, the velocity-amplifying impact resulting in an impacted second impact object having a velocity greater in magnitude than an initial velocity of the second impact object.

25. The shock apparatus of claim 24, comprising a velocity selection means for selecting the velocity produced by the velocity amplifying impact.

26. The shock apparatus of claim 25, wherein the velocity selection means comprises an impact portion having selectable properties, the impact portion being of at least one of: the first impact object or the second impact object.

27. The shock apparatus of claim 26, wherein the selectable properties include at least one of: a first material of a first impact portion of the first impact object, a second material of a second impact portion of the second impact object, a structure of the first impact portion of the first impact object, or a structure of the second impact portion of the second impact object.

* * * * *